US012766367B2

(12) United States Patent
Lee et al.

(10) Patent No.: US 12,766,367 B2
(45) Date of Patent: Oct. 20, 2026

(54) CARDIOPULMONARY REHABILITATION ASSISTANCE SYSTEM

(71) Applicants: METABRAIN TECHNOLOGY PTE. LTD., Singapore (SG); ZHUHAI ULOOK METABRAIN MEDICAL TECHNOLOGY CO., LTD., Zhuhai City (CN)

(72) Inventors: Shin-Da Lee, Taichung (TW); Yu-Chieh Huang, Taichung (TW)

(73) Assignees: METABRAIN TECHNOLOGY PTE. LTD., Singapore (SG); ZHUHAI ULOOK METABRAIN MEDICAL TECHNOLOGY CO., LTD., Zhuhai City (CN)

( * ) Notice: Subject to any disclaimer, the term of this patent is extended or adjusted under 35 U.S.C. 154(b) by 684 days.

(21) Appl. No.: 18/328,123

(22) Filed: Jun. 2, 2023

(65) Prior Publication Data

US 2024/0399210 A1 Dec. 5, 2024

(51) Int. Cl.
*A63B 24/00* (2006.01)
*A61M 16/00* (2006.01)
(Continued)

(52) U.S. Cl.
CPC ....... *A63B 24/0087* (2013.01); *A61M 16/024* (2017.08); *A61M 16/0875* (2013.01);
(Continued)

(58) Field of Classification Search
CPC ......... A61M 16/1005; A63B 2213/005; A63B 22/0605; A61B 5/08; A61B 5/082; A61B 5/087; A61B 5/091
See application file for complete search history.

(56) References Cited

U.S. PATENT DOCUMENTS

2016/0051847 A1* 2/2016 Zhang ................. A61M 16/101
128/202.13
2017/0274250 A1* 9/2017 Itoh ........................ A61B 5/742
(Continued)

FOREIGN PATENT DOCUMENTS

TW I788077 B 12/2022
WO WO-2005032664 A1 * 4/2005 ......... A63B 22/0605
(Continued)

*Primary Examiner* — Kendra D Carter
*Assistant Examiner* — Akhil A Jayan
(74) *Attorney, Agent, or Firm* — MUNCY, GEISSLER, OLDS & LOWE, P.C.

(57) ABSTRACT

A cardiopulmonary rehabilitation assistance system is provided, including: a training unit, an exercise assistance unit, a physiological biosignal-monitoring unit and a control unit. The training unit includes an ergometer, and the exercise assistance unit includes an intake tube, an oxygen supply module configured to supply oxygen to the intake tube. The physiological biosignal-monitoring unit includes a blood oxygen saturation sensor configured to measure a blood oxygen saturation of a user, and the control unit controls the ergometer to perform an assisted exercise program. In the assisted exercise program, the control unit performs at least one of a training assistance program and an exercise safety program to meet different requirements. In the training assistance program, the control unit controls the oxygen supply module to supply extra oxygen when the blood oxygen saturation is out of a suggested saturation range.

11 Claims, 4 Drawing Sheets

(51) Int. Cl.

| | |
|---|---|
| ***A61M 16/08*** | (2006.01) |
| ***A61M 16/16*** | (2006.01) |
| ***A63B 22/06*** | (2006.01) |
| ***A63B 71/00*** | (2006.01) |
| ***A63B 71/06*** | (2006.01) |

(52) U.S. Cl.
CPC ......... *A61M 16/16* (2013.01); *A63B 22/0605* (2013.01); *A63B 71/0622* (2013.01); *A61M 2202/0208* (2013.01); *A61M 2230/205* (2013.01); *A63B 2024/0068* (2013.01); *A63B 2024/0093* (2013.01); *A63B 2071/0081* (2013.01); *A63B 2071/0661* (2013.01); *A63B 2213/005* (2013.01); *A63B 2220/35* (2013.01); *A63B 2230/045* (2013.01); *A63B 2230/208* (2013.01)

(56) References Cited

U.S. PATENT DOCUMENTS

| | | | | |
|---|---|---|---|---|
| 2018/0056111 | A1* | 3/2018 | Chiang .............. | A63B 71/0619 |
| 2020/0269122 | A1* | 8/2020 | Zitvogel ............... | A63F 13/803 |
| 2020/0360690 | A1* | 11/2020 | Evans .................... | G16H 20/40 |
| 2021/0137467 | A1* | 5/2021 | Aoki ...................... | A61B 5/082 |
| 2022/0118315 | A1* | 4/2022 | Sankai ................... | A61B 5/222 |

FOREIGN PATENT DOCUMENTS

| | | | | | |
|---|---|---|---|---|---|
| WO | WO-2009129739 | A1 * | 10/2009 | .......... | A61M 16/101 |
| WO | WO-2016203664 | A1 * | 12/2016 | ............. | A63B 22/06 |
| WO | WO-2021010150 | A1 * | 1/2021 | ............. | A61B 5/091 |

* cited by examiner

CARDIOPULMONARY REHABILITATION ASSISTANCE SYSTEM

BACKGROUND OF THE INVENTION

Field of the Invention

The present invention relates to a cardiopulmonary rehabilitation assistance system.

Description of the Prior Art

Chronic obstructive pulmonary disease is a common chronic respiratory disease. With the change of population structure, air pollution and environmental change, a number of patients with chronic obstructive pulmonary disease has increased significantly. Therefore, how to reduce medical consumption and improve the quality of life of the patients has become an important issue in the medical field.

Generally, rehabilitation exercise is one of the most effective treatments to alleviate the deterioration of symptoms and improve the quality of life. However, the purpose of rehabilitation exercise may not easily achieve due to the intolerance of the patient, and other exercise assistance methods are still required. A conventional rehabilitation exercise assistance method is to directly supply extra oxygen, positive pressure air or drug to a patient's respiratory system for supporting so as to increase the load intensity of the rehabilitation exercise. However, how to supply oxygen, positive pressure air or drug at appropriate time and dosage are still researching.

The present invention is, therefore, arisen to obviate or at least mitigate the above-mentioned disadvantages.

SUMMARY OF THE INVENTION

The main object of the present invention is to provide a cardiopulmonary rehabilitation assistance system to overcome the above-mentioned disadvantages.

To achieve the above and other objects, the present invention provides a cardiopulmonary rehabilitation assistance system, including: a training unit, an exercise assistance unit, a physiological biosignal-monitoring unit and a control unit.

The training unit includes an adjustable load intensity ergometer configured for a user to ride. The exercise assistance unit includes an intake tube near the user and an oxygen supply module communicated with the intake tube and configured to supply oxygen to the intake tube. The physiological biosignal-monitoring unit includes a blood oxygen saturation sensor configured to measure a blood oxygen saturation of the user. The control unit is electrically connected with the ergometer, the oxygen supply module and the blood oxygen saturation sensor, and the control unit controls the ergometer to perform an assisted exercise program. In the assisted exercise program, the ergometer adjusts the load intensity according to a predetermined resistance given protocol. During the assisted exercise program, the control unit performs at least one of a training assistance program and an exercise safety program. In the training assistance program, the control unit controls the oxygen supply module to supply extra oxygen when the blood oxygen saturation is out of a suggested saturation range; and in the exercise safety program, the control unit controls the ergometer to reduce the load intensity or stop when the blood oxygen saturation is lower than a critical saturation value.

The advantage of the present invention is that: with the training unit, the exercise assistance unit, the physiological biosignal-monitoring unit and the control unit, the present invention can assist the user in cardiopulmonary rehabilitation, the assisted exercise program helps to enhance the rehabilitation efficiency, and the exercise safety program ensures the safety of the user.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
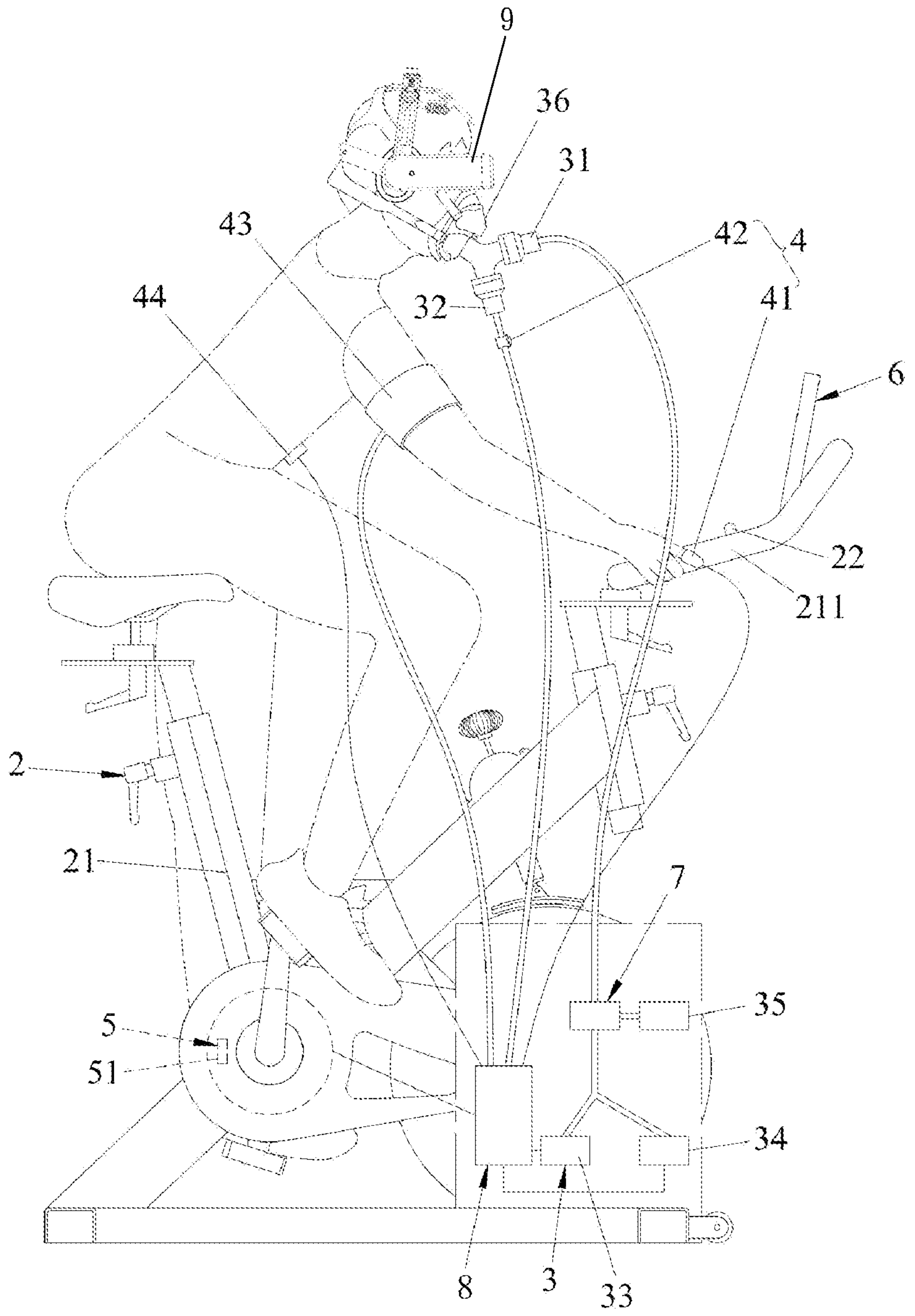
FIG. 1 is a schematic diagram showing operation of a preferable embodiment of the present invention.
Figure 2:
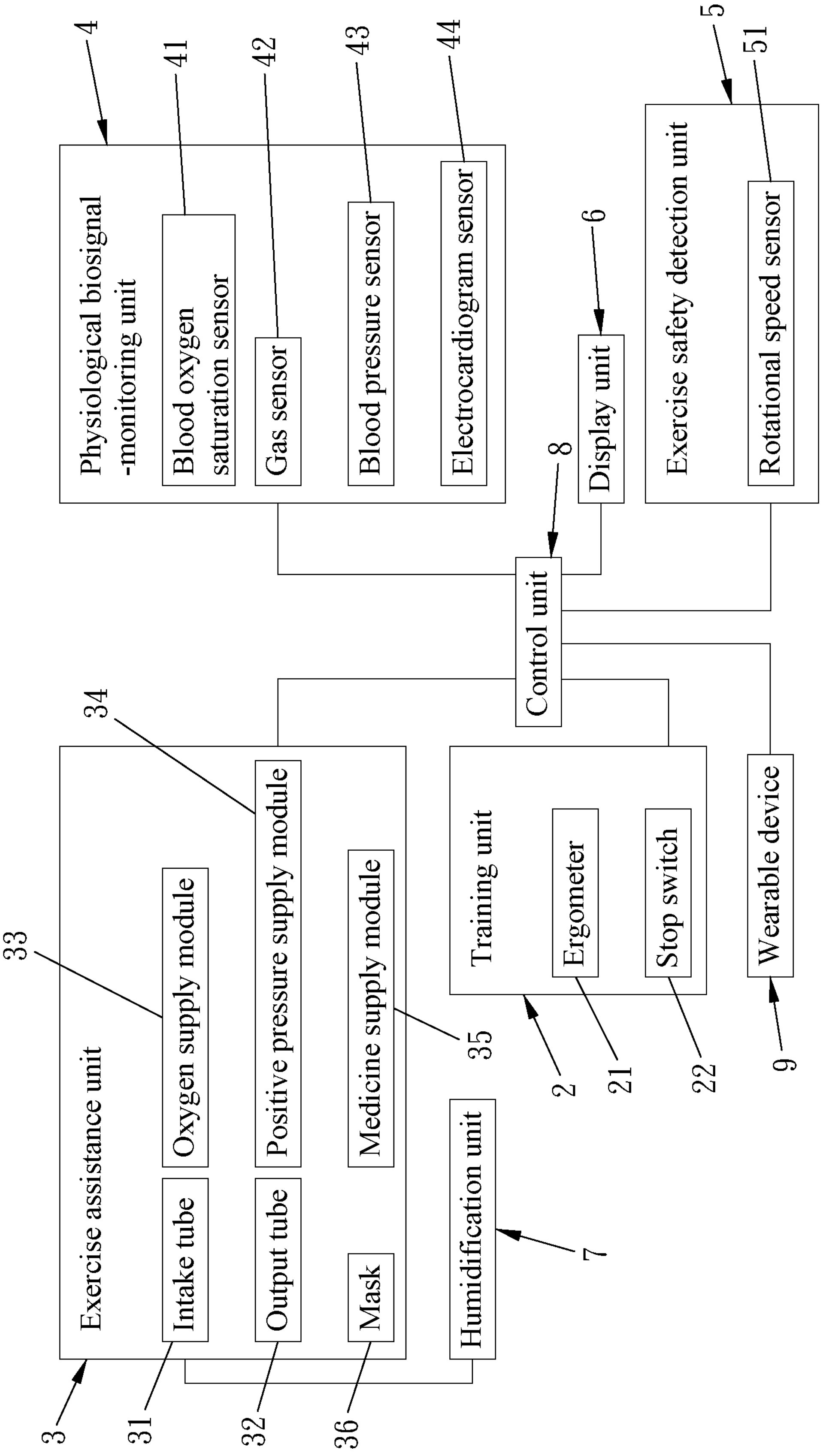
FIG. 2 is a block diagram of a preferable embodiment of the present invention.

Please refer to FIGS. 1 to 2 for a preferable embodiment of the present invention. A cardiopulmonary rehabilitation assistance system of the present invention includes a training unit 2, an exercise assistance unit 3, a physiological biosignal-monitoring unit 4, an exercise safety detection unit 5, a display unit 6, a humidification unit 7 and a control unit 8.

The training unit 2 includes an ergometer 21 configured for a user to ride and being controllable to adjust a load intensity and a stop switch 22. In this embodiment, the ergometer 21 includes a handle 211 and a driving motor (not shown in the figures), and the load intensity of the ergometer 21 is determined by a resistance exerted by the driving motor. The stop switch 22 is disposed on the handle 211, but not limited to, the stop switch 22 may be disposed on other positions of the ergometer 21 for easy operation.

The exercise assistance unit 3 includes an intake tube 31 near the user, an output tube 32 near the user, an oxygen supply module 33 communicated with the intake tube 31 and configured to supply oxygen to the intake tube 31, a positive pressure air supply module 34 communicated with the intake tube 31 and configured to supply gas to the intake tube 31, and a medicine supply module 35 configured to supply a medicine spray to the intake tube 31. In this embodiment, the oxygen supply module 33 is an oxygen generator or an oxygen tank; the positive pressure air supply module 34 is a non-invasive ventilation; the medicine spray is a bronchodilator used to dilate the bronchi; and the intake tube 31 and the output tube 32 are disposed on a mask 36 configured for the user to wear.

The physiological biosignal-monitoring unit 4 includes a blood oxygen saturation sensor 41 configured to measure a blood oxygen saturation of the user, a gas sensor 42 configured to sense changes of a gas flow in the output tube 32, a blood pressure sensor 43 configured to measure a blood pressure of the user, and an electrocardiogram (ECG) sensor 44 configured to measure ECG signals of the user. In this embodiment, the blood oxygen saturation sensor 41 is disposed on a finger of the user to measure the blood oxygen saturation, and the gas sensor 42 is a gas flow meter disposed on a connecting pipe communicated with the output tube 32.

The exercise safety detection unit 5 includes a rotational speed sensor 51 disposed on the ergometer 21 and configured to detect a rotational speed of the ergometer 21.

The display unit 6 is disposed on the ergometer 21. In this embodiment, the display unit 6 may display a prompt message, the rotational speed of the ergometer 21, a heart rate of the user, the blood pressure of the user, notice of arrhythmia, statistics information of exercise performance, or any other information.

The humidification unit 7 is configured to supply a water vapor with a constant temperature to the intake tube 31. In this embodiment, the humidification unit 7 automatically provides the water vapor with the constant temperature. In other embodiments, the gas provided by any other components may be humidified before passing through the intake tube 31.

The control unit 8 is electrically connected with the ergometer 21, the stop switch 22, the oxygen supply module 33, the positive pressure air supply module 34, the medicine supply module 35, the blood oxygen saturation sensor 41, the gas sensor 42, the blood pressure sensor 43, the electrocardiogram sensor 44, the rotational speed sensor 51 and the display unit 6. The control unit 8 controls the ergometer 21 to perform an assisted exercise program. In the assisted exercise program, the ergometer 21 adjusts the load intensity according to a predetermined resistance given protocol. The control unit 8 controls the ergometer 21 to stop when the stop switch 22 is triggered.

In the assisted exercise program, the predetermined resistance given protocol represents the load intensity of the ergometer 21 at a plurality of exercise stages during an exercise period, and each of the plurality of exercise stages corresponds to a preset rotational speed. In one preferable embodiment, the control unit 8 controls the load intensity of the ergometer 21 to be gradually increased with the plurality of exercise stages in sequence during the exercise period, and the predetermined resistance given protocol may be changed to meet different requirements.

In the assisted exercise program, the control unit 8 performs at least one of a training assistance program and an exercise safety program according to different circumstances.

In the training assistance program, the control unit 8 performs following two steps.

First, the control unit 8 controls the oxygen supply module 33 to supply extra oxygen when the blood oxygen saturation is out of a suggested saturation range.

Figure 3:
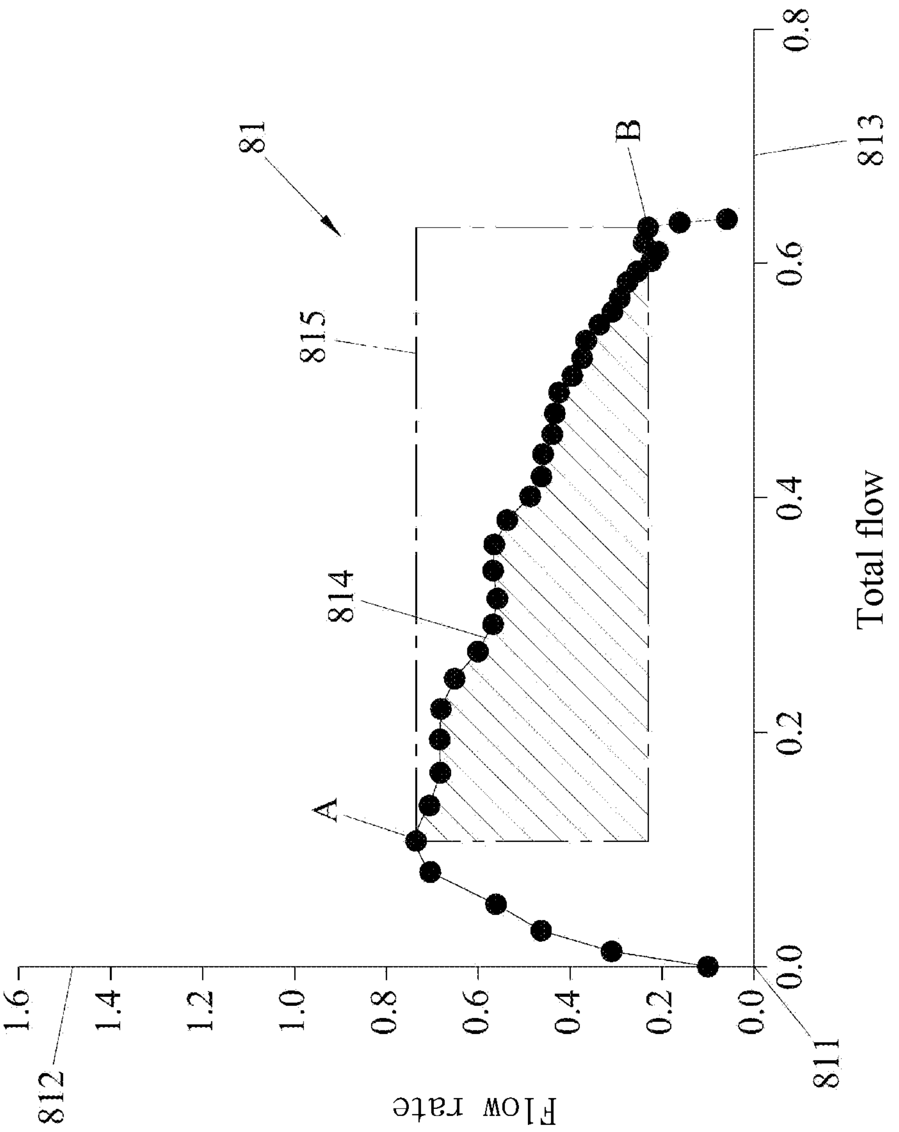
FIG. 3 is an exhalation flow chart of a preferable embodiment of the present invention.
Figure 4:
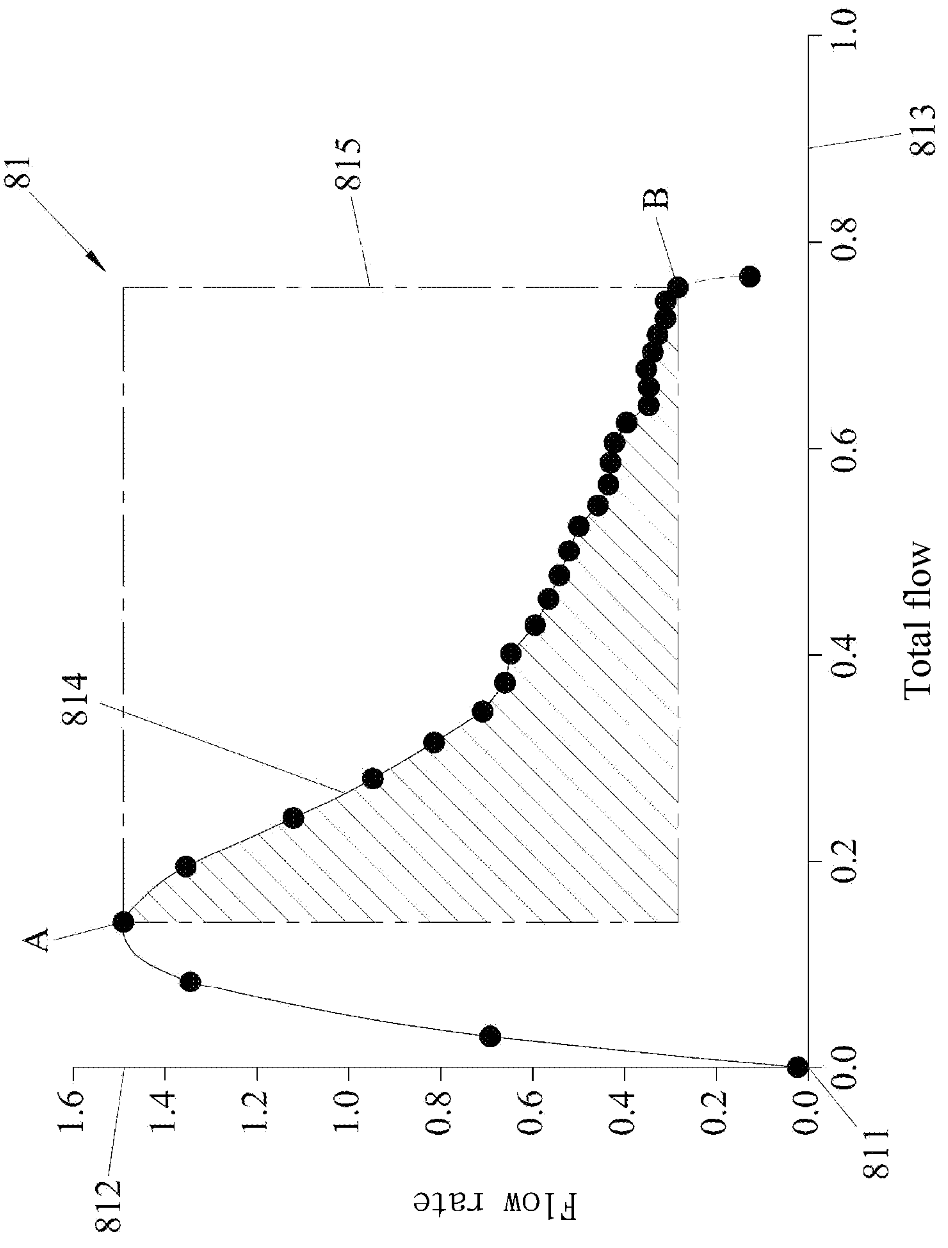
FIG. 4 is another exhalation flow chart of a preferable embodiment of the present invention.

Second, please refer to FIGS. 2-4, the control unit 8 generates a positive pressure supply based on an analysis of an exhalation flow chart 81 generated according to the changes of the gas flow sensed by the gas sensor 42. The exhalation flow chart 81 includes a vertical axis 812 representing a flow rate of the gas flow, a horizontal axis 813 representing a flow volume of the gas flow, a coordinate zero point 811 connected the vertical axis 812 with the horizontal axis 813, and an exhalation curve 814 located at a first quadrant of a coordinate plane defining by the vertical axis 812 and the horizontal axis 813. The control unit 8 calculates a rectangular area ratio according to the exhalation curve 814. A rectangular region 815 is defined by a highest point A near a starting point on a left side of the exhalation curve 814 and a terminal point B on a right side of the exhalation curve 814, and the rectangular area ratio is a ratio of an area defined between the exhalation curve 814 and edges of the rectangular region 815 adjacent to the coordinate zero point 811 (the hatching area in FIGS. 3-4) to an overall area of the rectangular region 815. The control unit 8 controls the positive pressure air supply module 34 to supply a positive gas pressure to the intake tube 31 when the rectangular area ratio is lower than a preset ratio.

After the control unit 8 controls the positive pressure air supply module 34 to supply the positive gas pressure to the intake tube 31, the control unit 8 controls the medicine supply module 35 to supply the medicine spray to the intake tube 31 when the rectangular area ratio is still lower than the preset ratio.

Please refer to FIGS. 1 and 2, in the exercise safety program, the control unit 8 performs following four steps.

First, the control unit 8 controls the ergometer 21 to reduce the load intensity or stop when the blood oxygen saturation is lower than a critical saturation value.

Second, when the rotational speed sensor 51 senses the rotational speed of the ergometer 21 is lower than the preset rotational speed corresponding to one of the plurality of exercise stages being performed, the control unit 8 controls the load intensity of the ergometer 21 to remain unchanged or reduce in next one of the plurality of exercise stages.

Third, the control unit 8 controls the ergometer 21 to reduce the load intensity or stop when the control unit 8 determines that the user is in a blood pressure abnormal status according to the blood pressure measured by the blood pressure sensor 43.

Forth, the control unit 8 controls the ergometer 21 to reduce the load intensity or stop when the control unit 8 determines that the user is in a ECG abnormal status according to the ECG signals measured by the electrocardiogram sensor 44.

Specifically, the electrical connection mentioned in the present invention may refer to wired or wireless connection. Therefore, signal transmission between the blood oxygen saturation sensor 41, the gas sensor 42, the blood pressure sensor 43, the electrocardiogram sensor 44 and the rotational speed sensor 51 may be wired or wireless signal transmission.

In operation, the user wears the mask 36, the blood oxygen saturation sensor 41, the blood pressure sensor 43 and the electrocardiogram sensor 44 and rides the ergometer 21 for cardiopulmonary rehabilitation. During rehabilitation exercise, the control unit 8 performs the assisted exercise program. In this embodiment, the exercise period is 30 minutes; a number of the plurality of exercise stages is ten; each of the plurality of exercise stages is 3 minutes long, and the preset rotational speed is 40 rpm and may be increased gradually. Preferably, the cardiopulmonary rehabilitation assistance system further includes a wearable device 9, and the wearable device 9 is communicated with the control unit 8 and configured to display a virtual image. The wearable device 9 may be an augmented reality (AR) device or a virtual reality (VR) device, which provides the user with a real and rich riding experience.

In the assisted exercise program, the control unit 8 controls the load intensity of the ergometer 21 to be gradually increased with the plurality of exercise stages in sequence during the exercise period so that the user can train cardiorespiratory function and increase exercise endurance with the increase of the load intensity. In this embodiment, the load intensity of the ergometer 21 in the plurality of exercise stages is sequentially increased 20 watts per exercise stage.

During exercise, when the control unit 8 determines that physiological parameters of the user are abnormal or the rotational speed sensed by the rotational speed sensor 51 is lower than the preset rotational speed and the load intensity cannot be gradually increased, the control unit 8 performs the exercise safety program. Four steps of the exercise safety program are described below.

First, when the control unit 8 controls the ergometer 21 to reduce the load intensity or stop when the blood oxygen saturation of the user sensed by the blood oxygen saturation sensor 41 is lower than the critical saturation value. When the load intensity is unchanged, the user exercises under a maximum load intensity being endurable under the current physiological parameters. In this embodiment, the critical saturation value is 88%.

Second, the control unit 8 controls the display unit 6 to display a low-speed prompt when the rotational speed sensor 51 senses the rotational speed of the ergometer 21 is lower than corresponding one of said preset rotational speeds. The low-speed prompt may be a prompt message for asking the user to speed up so as to encourage the user to continue exercising hard. When the rotational speed sensed by the rotational speed sensor 51 has been continuously lower than the preset rotational speed, it means that the user cannot increase the load intensity, and the control unit 8 controls the load intensity of the ergometer 21 to remain unchanged or reduce or controls the ergometer 21 to stop.

Third, the control unit 8 controls the load intensity of the ergometer 21 to remain unchanged or reduce or controls the ergometer 21 to stop when the control unit 8 determines that the user is in the blood pressure abnormal status according to the blood pressure sensed by the blood pressure sensor 43. When the load intensity remains unchanged, the user exercises under a maximum load intensity being endurable under the current physiological parameters. Specifically, the blood pressure abnormal status refers that the systolic or diastolic blood pressure of the user during exercise is much higher than the blood pressure measured before exercise. For example, the systolic blood pressure is higher than 180 mmHg or diastolic blood pressure is higher than 110 mmHg; the systolic blood pressure of the user measured in the present exercise stage is much higher than the systolic blood pressure measured in the previous exercise stage (e.g. 20 mmHg higher than the previous exercise stage); or the diastolic blood pressure of the user measured in the present exercise stage is much lower than the diastolic blood pressure measured in the previous exercise stage (e.g. 20 mmHg lower than the previous exercise stage).

Fourth, the control unit 8 controls the load intensity of the ergometer 21 to remain unchanged or reduce or controls the ergometer 21 to stop when the control unit 8 determines that the user is in the ECG abnormal status according to the ECG signals sensed by the electrocardiogram sensor 44. When the load intensity remains unchanged, the user exercises under a maximum load intensity being endurable under the current physiological parameters. The ECG abnormal status refers to arrhythmia, and the diagnosis of arrhythmia is an existing technology and will not be further described.

A process of the control unit 8 performing the training assistance program is described as follow.

The control unit 8 controls the oxygen supply module 33 to supply extra oxygen to the intake tube 31 when the blood oxygen saturation sensed by the blood oxygen saturation sensor 41 is out of the suggested saturation range so that the blood oxygen saturation of the user is improved to bear the exercise load. In this embodiment, the suggested saturation range is between 90% and 92%, and the gas supplied by the oxygen supply module 33 may be pure oxygen or a mixed gas containing oxygen. For example, the mixed gas may include 60% of oxygen, 40% of nitrogen and 25 ppm nitric oxide; the mixed gas may include 60% of oxygen, 40% of nitrogen and 40 ppm nitric oxide; the mixed gas may include 28% of oxygen and 72% of nitrogen, or the mixed gas may include 21% of oxygen and 79% of nitrogen, but not limited thereto.

Please refer to FIGS. 2, 3 and 4, the control unit 8 generates the exhalation flow chart according to the changes of the gas flow sensed by the gas sensor 42. The control unit 8 controls the positive pressure air supply module 41 to supply the positive gas pressure to the intake tube 31 when the rectangular area ratio is lower than the preset ratio so that the user can breathe more easily and bear the exercise load. In this embodiment, the preset ratio is 0.5.

After the control unit 8 controls the positive pressure air supply module 41 to supply the positive gas pressure to the intake tube 31 and controls the oxygen supply module 33 to supply oxygen, the control unit 8 controls the medicine supply module 35 to supply the medicine spray to the intake tube 31 when the rectangular area ratio is still lower than the preset ratio. As such, when supplementations with oxygen and the positive pressure gas are ineffective to the user, the medicine spray can be automatically provided to the user and the user can breathe more easily and bear the exercise load.

Since the load intensity of the ergometer 21 can be adjusted sequentially and increased gradually, the cardiorespiratory function and the aerobic capacity of the user can be trained to improve exercise endurance and quality of life. Moreover, providing oxygen, the positive pressure gas and the medicine spray according to the physiological parameters of the user can increase the exercise endurance of the user so that the lung function can be effectively improved to achieve good rehabilitation effect.

Furthermore, when the user feels uncomfortable, the user can actuate the stop switch 22 to stop the ergometer 21, which ensures the safety of the user. With the exercise safety program, the control unit 8 can adjust the load intensity according to the physiological parameters of the user, which also increases operational safety.

In summary, with the training unit 2, the exercise assistance unit 3, the physiological biosignal-monitoring unit 4, the exercise safety detection unit 5 and the control unit 8, the present invention can assist the user in cardiopulmonary rehabilitation, the assisted exercise program helps to increase the rehabilitation efficiency, and the exercise safety program ensures the safety of the user.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A cardiopulmonary rehabilitation assistance system, including:

a training unit, including a ergometer configured for a user to ride and being controllable to adjust a load intensity;

an exercise assistance unit, including an intake tube near the user and an oxygen supply module communicated with the intake tube and configured to supply oxygen to the intake tube;

a physiological biosignal-monitoring unit, including a blood oxygen saturation sensor configured to measure a blood oxygen saturation of the user; and a control unit, electrically connected with the ergometer, the oxygen supply module and the blood oxygen saturation sensor, controlling the ergometer to perform an assisted exercise program;

wherein in the assisted exercise program, the ergometer adjusts the load intensity according to a predetermined resistance given protocol, during the assisted exercise program, the control unit performs at least one of a training assistance program and an exercise safety program; in the training assistance program, the control unit controls the oxygen supply module to supply extra oxygen when the blood oxygen saturation is out of a suggested saturation range; and in the exercise safety program, the control unit controls the ergometer to reduce the load intensity or stop when the blood oxygen saturation is lower than a critical saturation value;

wherein the exercise assistance unit further includes an output tube configured to be near the user and a positive pressure air supply module communicated with the intake tube and configured to supply gas to the intake tube, and the physiological biosignal-monitoring unit further includes a gas sensor configured to sense changes of a gas flow in the output tube;

wherein in the training assistance program, the control unit generates a positive pressure supply based on an analysis of an exhalation flow chart generated according to the changes of the gas flow sensed by the gas sensor, the exhalation flow chart includes a vertical axis representing a flow rate of the gas flow, a horizontal axis representing a total flow of the gas flow, a coordinate zero point connecting the vertical axis with the horizontal axis, and an exhalation curve located at a first quadrant of a coordinate plane defined by the vertical axis and the horizontal axis, the control unit calculates a rectangular area ratio according to the exhalation curve, a rectangular region is defined by a highest point near a starting point on a left side of the exhalation curve and a terminal point on a right side of the exhalation curve, the rectangular area ratio is a ratio of an area defined between the exhalation curve and edges of the rectangular region adjacent to the coordinate zero point to an overall area of the rectangular region, and the control unit controls the positive pressure air supply module to supply a positive gas pressure to the intake tube when the rectangular area ratio is lower than a preset ratio.

2. The cardiopulmonary rehabilitation assistance system of claim 1, wherein the exercise assistance unit further includes a medicine supply module electrically connected with the control unit and configured to supply a medicine spray to the intake tube, after the control unit controls the positive pressure air supply module to supply the positive gas pressure to the intake tube, the control unit controls the medicine supply module to supply the medicine spray to the intake tube when the rectangular area ratio is still lower than the preset ratio.

3. The cardiopulmonary rehabilitation assistance system of claim 1, further including an exercise safety detection unit, wherein the exercise safety detection unit includes a rotational speed sensor disposed on the ergometer and electrically connected with the control unit to detect a rotational speed of the ergometer, and in the assisted exercise program, the predetermined resistance given protocol represents the load intensity of the ergometer at a plurality of exercise stages during an exercise period.

4. The cardiopulmonary rehabilitation assistance system of claim 3, wherein each of the plurality of exercise stages corresponds to a preset rotational speed, and in the exercise safety program, when the rotational speed sensor senses the rotational speed of the ergometer is lower than the preset rotational speed corresponding to one of the plurality of exercise stages being performed, the control unit controls the load intensity of the ergometer to remain unchanged or reduce in next one of the plurality of exercise stages.

5. The cardiopulmonary rehabilitation assistance system of claim 3, wherein the control unit controls the load intensity of the ergometer to be gradually increased with the plurality of exercise stages in sequence during the exercise period.

6. The cardiopulmonary rehabilitation assistance system of claim 3, further including a display unit disposed on the ergometer, wherein the control unit controls the display unit to display a low-speed prompt when the rotational speed sensor senses the rotational speed of the ergometer is lower than corresponding one of said preset rotational speeds.

7. The cardiopulmonary rehabilitation assistance system of claim 1, wherein the physiological biosignal-monitoring unit further includes a blood pressure sensor configured to measure a blood pressure of the user, and in the exercise safety program, the control unit controls the ergometer to reduce the load intensity or stop when the control unit determines that the user is in a blood pressure abnormal status according to the blood pressure measured by the blood pressure sensor.

8. The cardiopulmonary rehabilitation assistance system of claim 1, wherein the physiological biosignal-monitoring unit further includes an electrocardiogram (ECG) sensor configured to measure ECG signals of the user, and in the exercise safety program, the control unit controls the ergometer to reduce the load intensity or stop when the control unit determines that the user is in a ECG abnormal status according to the ECG signals measured by the electrocardiogram sensor.

9. The cardiopulmonary rehabilitation assistance system of claim 1, further including a humidification unit, wherein the humidification unit is configured to supply a water vapor with a constant temperature to the intake tube.

10. The cardiopulmonary rehabilitation assistance system of claim 1, wherein the training unit further includes a stop switch electrically connected with the control unit, and the control unit controls the ergometer to stop when the stop switch is triggered.

11. The cardiopulmonary rehabilitation assistance system of claim 1, further including a wearable device, wherein the wearable device is communicated with the control unit and configured to display a virtual image.

* * * * *